United States Patent [19]  [11] 4,125,564
Iwasaki et al.  [45] Nov. 14, 1978

[54] PROCESS FOR PRODUCING CHLOROPRENE

[75] Inventors: Takao Iwasaki; Junji Hirano, both of Ohmi; Hideki Matsumura, Machida, all of Japan

[73] Assignee: Denki Kagaku Kogyo Kabushiki Kaisha, Chuo-Kenkyusho, Tokyo, Japan

[21] Appl. No.: 847,930

[22] Filed: Nov. 2, 1977

[51] Int. Cl.² ............................................. C07C 21/20
[52] U.S. Cl. ................................. 260/655; 260/654 S; 260/654 H
[58] Field of Search ........... 260/654 H, 654 S, 654 R, 260/655

[56] References Cited

U.S. PATENT DOCUMENTS 3,850,999  11/1974  Gehrmann et al. ............. 260/654 H
3,898,294  8/1975  Cooley ................................. 260/655

Primary Examiner—Delbert E. Gantz
Assistant Examiner—Joseph A. Boska
Attorney, Agent, or Firm—Oblon, Fisher, Spivak, McClelland & Maier

[57] ABSTRACT

Chloroprene is produced by reacting 3,4-dichlorobutene-1 with a base in the presence of thiodiphenyl amine and 2,6-di-tertiarybutyl-p-cresol and preventing clogging of the equipment.

3,4-Dichlorobutene-1 is produced by an isomerization of the reaction mixture obtained by a chlorination of excess of butadiene wherein higher boiling compounds are separated before a separation of the unreacted butadiene.

6 Claims, No Drawings

PROCESS FOR PRODUCING CHLOROPRENE

BACKGROUND OF THE INVENTION

1. Field of the Invention

The present invention relates to a process for producing chloroprene and preventing a clogging of an equipment in the steps. More particularly, it relates to produce chloroprene under preventing the clogging by a separation of higher boiling compounds from a reaction mixture of a chlorination of butadiene or a formation of polymers.

2. Description of the Prior Arts

Chloroprene can be produced by chlorinating excess of butadiene to prepare a reaction mixture containing 3,4-dichlorobutene-1 and 1,4-dichlorobutene-2 and separating the unreacted butadiene and isomerizing 1,4-dichlorobutene-2 to 3,4-dichlorobutene-1 and converting 3,4-dichlorobutene to chloroprene by a dehydrogenchlorization.

During the operation, higher boiling compounds and polymers of chloroprene are formed to cause a clogging of an equipment.

SUMMARY OF THE INVENTION

It is an object of the present invention to provide a process for producing chloroprene without a clogging of an equipment in the production of 3,4-dichlorobutene-1.

It is another object of the present invention to provide a process for producing chloroprene by preventing a formation of a polymer of chloroprene.

The foregoing objects have been attained by separating the higher boiling compounds formed in the chlorination of excess of butadiene, before separating the unreacted butadiene in the step of producing 3,4-dichlorobutene-1 and if necessary, preventing the formation of the polymers by converting 3,4-dichlorobutene-1 to chloroprene with a base in the presence of thiodiphenyl amine and 2,6-di-tertiarybutyl-p-cresol.

DETAILED DESCRIPTION OF THE PREFERRED EMBODIMENTS 3,4-Dichlorobutene-1 is produced by chlorinating excess of butadiene to form the reaction mixture containing 3,4-dichlorobutene-1 and 1,4-dichlorobutene-2, separating the unreacted butadiene from the reaction mixture and isomerizing 1,4-dichlorobutene-2 to 3,4-dichlorobutene-1.

In the process of the present invention, the higher boiling compounds such as tars and carbonized materials, tetrachlorobutane and pentachlorobutane in the reaction mixture are separated before the separation of the unreacted butadiene and the isomerization of 1,4-dichlorobutene.

When the mixture of 3,4-dichlorobutene-1 and 1,4-dichlorobutene-2 is produced by the chlorination of butadiene, the by-products of trichlorobutene, tetrachlorobutane, pentachlorobutane, chloroprene, 1-chlorobutadiene-1,3, monochlorobutene, dichlorobutane etc., are formed and the tars and the carbonized materials are also formed. In the reaction mixture resulted by the chlorination of butadiene, the unreacted butadiene and these reaction mixture are contained. When 1,4-dichlorobutene-2 in the reaction mixture is isomerized to 3,4-dichlorobutene-1, it is preferable to separate and to recover the unreacted butadiene and also to separate the higher boiling compounds having a boiling point of higher than that of tetrachlorobutane.

When the unreacted butadiene is firstly recovered from the reaction product and then, the higher boiling compounds are separated, the equipments of the butadiene-separation device and the higher boiling compounds-separation device may be clogged and the operation could not be continued.

In the process of British Pat. No. 984,094, the isomerization is carried out after separating butadiene from the reaction mixture produced by the chlorination of butadiene and then, separating the higher boiling compounds. In the known process, the butadiene-separation device and the higher boiling compounds-separation device are easily clogged.

In accordance with the process of the present invention, the recovery of butadiene is carried out after separating the higher boiling compounds comprising mainly the tars, the carbonized materials and small amounts of tetrachlorobutane and pentachlorobutane and the isomerization of 1,4-dichlorobutene-2 is carried out after recovering the unreacted butadiene. After receeovering butadiene, the higher boiling compounds comprising mainly trichlorobutene are preferably separated before or during the isomerization of 1,4-dichlorobutene-2. The higher boiling compounds comprising the tars and the carbonized materials can be easily attained by passing the reaction mixture through a heat exchanger to cool it and to condense and to separate the higher boiling compounds.

In accordance with the process, the isomerization of 1,4-dichlorobutene-2 can be effectively continued for a long time without any clogging.

3,4-Dichlorobutene-1 having high purity can be obtained by separating the lower boiling materials such as chloroprene, 1-chlorobutadiene-1,3, monochlorobutene, and dichlorobutane. The higher boiling compounds can be separated before the recovery of the unreacted butadiene by a simple separation with a distillation tower, or a condensation with a heat exchanger. The amount of the higher boiling compounds which should be separated before the recovery of butadiene is more than 20% preferably more than 50%.

The following is one example of the composition of the reaction mixture resulted by the chlorination of excess of butadiene.

| No. | Compound | Wt. % | b.p. (° C) | Note |
|---|---|---|---|---|
| 1 | HCl | 5.2 | — | |
| 2 | butadiene | 63.4 | −4.4 | |
| 3 | 3-chlorobutene-1 | } 0.05 | 64.1 | |
| 4 | 1-chlorobutene-2 | | 85.0 | |
| 5 | 2-chlorobutadiene-1,3 | } 0.05 | 59.4 | chloroprene |
| 6 | 4-chlorobutadiene-1,2 | | 88.0 | |
| 7 | 1-chlorobutadiene-1,3 | 0.15 | 68.0 | |
| 8 | 2,3-dichlorobutane | 0.05 | 116–120 | |
| 9 | 3,4-dichlorobutene-1 | 11.1 | 115 | |

-continued

| No. | Compound | Wt. % | b.p. (° C) | Note |
|---|---|---|---|---|
| 10 | cis 1,4-dichlorobutene-2 | 4.8 | 153 | relatively higher boiling compounds |
| 11 | trans 1,4-dichlorobutene-2 | 13.7 | 159 | |
| 12 | 1,2,4-trichlorobutene-3 | 0.15 | 180–190 | |
| 13 | 1,2,4-trichlorobutene-2 | 0.05 | 187 | |
| 14 | 1,2,3,4-tetrachlorobutane | 0.1 | 204–231 | higher boiling compounds |
| 15 | pentachlorobutane | 0.3 | >210 | |
| 16 | higher boiling compounds over pentachlorobutane | 0.3 | >215 | |
| 17 | tars | 0.4 | | |
| 18 | Carbonized materials | 0.2 | | |

No. 16 Higher boiling compounds over pentachlorobutane

The compounds No. 16 include dimer of 2-chlorobutadiene, dimer of dichlorobutene, chlorinated dimer of butadiene and highly chlorinated butane (more than 6 chlorine atoms).

The higher boiling compounds No. 14 to 18 which have a boiling points of higher than 200° C. should be separated before the separation of butadiene.

The relatively higher boiling compounds such as the compounds Nos. 12 and 13 need not be separated before the separation of butadiene and can be separated during or after the isomerization.

The lower boiling compounds such as monochlorobutene can be separated during or after the isomerization. Hydrogen chloride is mainly separated together with butadiene and the remainder may be separated during or after the isomerization.

The important feature of the present invention is to produce chloroprene by converting 3,4-dichlorobutene-1 with a base in the presence of thiodiphenyl amine and 2,6-di-tertiarybutyl-p-cresol.

It has been known that chloroprene is produced by reacting 3,4-dichlorobutene-1 with a base. In the continuous operation, polymers are formed to clog the equipment during the operation. The polymers are insoluble and are not easily separated. The equipment should be disassembled to remove the deposited polymers.

In accordance with the process of the present invention, thiodiphenyl amine and 2,6-di-tertiarybutyl-p-cresol are added in the conversion of 3,4-dichlorobutene-1 with a base to chloroprene, whereby the formation of the polymers is effectively prevented and the operation is remarkably stabilized to continue the operation for a long time.

The amount of thiodiphenyl amine is usually in a range of 0.01 to 1 wt.% preferably 0.05 to 0.5 wt.% to 3,4-dichlorobutene-1.

The amount of 2,6-di-tertiarybutyl-p-cresol is usually in a range of 0.01 to 1 wt.% preferably 0.05 to 0.5 wt.% to 3,4-dichlorobutene-1.

When only thiodiphenyl amine is added, the effect of stabilization is not enough. When only 2,6-di-tertiarybutyl-p-cresol is added, the effect of stabilization is not substantially found. The effect of stabilization can be imparted by combining them. These stabilizers are preferably admixed with 3,4-dichlorobutene-1 before the conversion.

The reaction of dehydrogen chlorination is usually carried out by mixing a base with 3,4-dichlorobutene-1.

The amount of the base is the stoichiometric amount or more to 3,4-dichlorobutene-1.

Suitable bases include alkali metal hydroxides, ammonia and ammonium hydroxide. It is preferable to use an aqueous solution of an alkali metal hydroxide. The reaction temperature is preferably in a range of 60° to 130° C.

The present invention will be further illustrated by certain examples.

EXAMPLE 1

A chlorination of butadiene was carried out by using excess of butadiene to obtain the reaction mixture containing 63.4 wt.parts of butadiene, 29.6 wt.parts of dichlorobutene, 0.3 wt.parts of lower boiling compounds such as monochlorobutadiene, 0.2 wt. parts of trichlorobutene, 1.3 wt.parts of higher boiling compounds such as tetrachlorobutane and tars and hydrochloric acid.

The reaction mixture was passed through a shell-and tube heat exchanger at a rate of 100 wt.parts/hour to condense and to separate dichlorobutene at a rate of 5.3 wt.parts/hour, trichlorobutene at a rate of 0.1 wt.part/hour and higher boiling compound such as tetrachlorobutane and tars at a rate of 0.9 wt.part/hour. The residual reaction product gas was fed to a butadiene-separation tower to separate unreacted butadiene and the residue of the reaction product was fed into a higher boiling compound-separation tower which was kept in the reduced pressure of 50 mmHg whereby the higher boiling compounds of trichlorobutene, tetrachlorobutane and tars were removed. The resulting 3,4-dichlorobutene which did not substantially contain the higher boiling compounds was fed into an isomerization tower to recover 3,4-dichlorobutene-1 by the distillation, and dichlorobutene is isomerized to produce 3,4-dichlorobutene-1 at a rate of 17.6 wt.parts/hour.

The operation was continued for 2 months, however, there was no trouble nor a tendancy of a clogging of the butadiene-separation tower and the higher boiling compounds-separation tower.

Reference 1

In accordance with the process of Example 1 except eliminating the step of separating higher boiling compounds before the step of separating butadiene, the test was repeated. The butadiene-separation tower was clogged for about 2 months and the higher boiling compounds-separation tower was clogged for about 1 month.

EXAMPLE 2

In accordance with the process of Example 1, the higher boiling compounds were separated only by the shell-and tube heat exchange before the separation of butadiene without using the higher boiling compounds-separation tower, and the operation was continued to obtain 3,4-dichlorobutene-1 at a rate of 20.7 wt.parts/ hour. The operation was continued for 2 months however, the trouble of the clogging of the butadiene-separation tower was not found and the trouble in the isomerization tower was not found.

EXAMPLE 3

A chlorination of 1,3-butadiene was carried out by using excess of butadiene to obtain the reaction mixture containing 12.4 wt.% of 3,4-dichlorobutene-1, 19.8 wt.% of 1,4-dichlorobutene-2, 0.2 wt.% of trichlorobutene, 0.5 wt.% of tetrachlorobutane, 0.3 wt.% of pentachlorobutane, 2.5 wt.% of tars and carbonized materials and lower boiling compounds of the unreacted butadiene, hydrogen chloride and monochlorobutadiene.

The reaction mixture was passed through a shell-and tube heat exchanger having 7 m$^2$ of a heat exchange area at a rate of 247.7 kg/hour to cool the reaction mixture from 260° C. to 110° C. under the pressure of 900 mmHg (abs.). The higher boiling compounds of tars and carbonized materials and 8.3% of tetrachlorobutane and 6.9% of pentachlorobutane were condensed and separated at a rate of 7.2 kg/hour. The residual reaction product gas was fed to a butadiene-separation tower having 30 trays wherein the unreacted butadiene was separated from the reaction product gas. The separated butadiene was recycled to the reactor for the chlorination. The residue of the reaction product separated from butadiene was fed to a higher boiling compounds-separation tower which had a diameter of 300 mm and a height of 700 mm and was filled with Raschig rings having a diameter of 25 mm wherein the higher boiling compounds containing mainly trichlorobutene were separated under the pressure of 50 mmHg(abs). The resulting dichlorobutene mixture which did not substantially contain higher boiling compounds was fed to an isomerization tower having 25 trays wherein 3,4-dichlorobutene-1 was recovered by a distillation and 1,4-dichlorobutene was isomerized in the presence of a catalyst of cuprous chloride and amine hydrochloride to obtain 3,4-dichlorobutene.

The operation was continued for 1 month, however, there was no trouble of clogging of the butadiene-separation tower or the higher boiling compounds-separation tower. The isomerization was continued without any trouble.

When the higher boiling compounds were not separated by the heat exchanger before the separation of butadiene, the butadiene-separation tower was clogged for 20 days and the higher boiling compounds-separation tower was clogged for 15 days. The operation could not be continued.

EXAMPLE 4

In a reactor equipped with a reflux condenser, 700 wt.parts of 5% aqueous solution of sodium hydroxide, 100 wt.parts of 3,4-dichlorobutene-1, 0.05 wt.part of thiodiphenyl amine and 0.05 wt.part of 2,6-di-tertiarybutyl-p-cresol were charged and the mixture was heated at 95° C. in nitrogen atmosphere for 12 hours.

The organic phase and the solid phase of the reaction mixture were separated from water phase and 200 wt.parts of methanol was added to the organic phase and the solid phase. The solid phase was separated from the liquid phase and dried at 30° to 40° C. under the reduced pressure and the weight of the solid phase was measured to give 2.3 wt.parts to 100 wt.parts of 3,4-dichlorobutene-1.

Reference 2

In accordance with the process of Example 4 except eliminating both of thiodiphenyl amine and 2,6-di-tertiarybutyl-p-cresol or either of them, the reactions were respectively carried out and the weights of the solid phases were measured. The results are as follows.

| Additive | Amount of solid phase to 100 wt. parts of 3,4-dichlorobutene-1 |
| --- | --- |
| None | 17.3 wt. parts |
| thiodiphenyl amine (0.1 wt. part) | 5.2 wt. parts |
| 2,6-di-tertiarybutyl-p-cresol (0.1 wt. part) | 18.0 wt. parts |

What is claimed is:

1. In a process for producing chloroprene which comprises chlorinating excess of butadiene; separating the unreacted butadiene from the reaction mixture; isomerizing 1,4-dichlorobutene-2 to 3,4-dichlorobutene-1; reacting 3,4-dichlorobutene-1 with a base to obtain chloroprene, an improvement characterized by reacting 3,4-dichlorobutene-1 with a base in the presence of thiodiphenyl amine and 2,6-di-tertiarybutyl-p-cresol, whereby a clogging of an equipment is prevented.

2. A process according to claim 1 wherein a stoichiometric amount or more of the base, 0.01 to 1 wt.% of thiodiphenyl amine and 0.01 to 1 wt.% of 2,6-di-tertiarybutyl-p-cresol to 3,4-dichlorobutene-1 are used.

3. A process according to claim 1 wherein thiodiphenyl amine and 2,6-di-tertiarybutyl-p-cresol are dissolved in 3,4-dichlorobutene-1.

4. In a process for producing chloroprene which comprises chlorinating excess of butadiene; separating the unreacted butadiene from the reaction mixture; isomerizing 1,4-dichlorobutene-2 to 3,4-dichlorobutene-1; reacting 3,4-dichlorobutene-1 with a base to obtain chloroprene, an improvement characterized by separating higher boiling compounds from the reaction mixture before the separation of the unreacted butadiene whereby a clogging of an equipment is prevented.

5. A process according to claim 4 wherein the separation of the higher boiling compounds is carried out by passing the reaction mixture gas through a heat exchanger to cool the gas, before the separation of the unreacted butadiene.

6. A process according to claim 4 wherein a first separation of the higher boiling compounds is carried out by passing the reaction mixture gas through a heat exchanger before the separation of the unreacted butadiene and, after separation of said unreacted butadiene, a second separation of relatively higher boiling compounds is carried out by passing the reaction mixture gas through a separation tower.

* * * * *